US009310284B2

(12) United States Patent
Graham et al.

(10) Patent No.: US 9,310,284 B2
(45) Date of Patent: Apr. 12, 2016

(54) MUZZLE EXIT TESTER (71) Applicant: Honeywell International Inc., Morristown, NJ (US)

(72) Inventors: Jason Graham, White Bear Lake, MN (US); Owen D. Grossman, Golden Valley, MN (US)

(73) Assignee: Honeywell International Inc., Morris Plains, NJ (US)

( * ) Notice: Subject to any disclaimer, the term of this patent is extended or adjusted under 35 U.S.C. 154(b) by 158 days.

(21) Appl. No.: 14/189,777

(22) Filed: Feb. 25, 2014

(65) Prior Publication Data

US 2015/0241326 A1 Aug. 27, 2015

(51) Int. Cl.
*G01M 7/00* (2006.01)
*G01N 3/307* (2006.01)
*F41B 11/722* (2013.01)
*F42B 35/00* (2006.01)
*G01M 7/08* (2006.01)
(Continued)

(52) U.S. Cl.
CPC .............. *G01N 3/307* (2013.01); *F41B 11/681* (2013.01); *F41B 11/722* (2013.01); *F41B 11/723* (2013.01); *F41B 11/87* (2013.01); *F42B 35/00* (2013.01); *G01M 7/08* (2013.01)

(58) Field of Classification Search
CPC ............. G01N 3/07; G01N 3/30; G01M 7/08; G01M 17/04; G01L 3/24
USPC ................ 73/12.11, 12.09, 12.01, 11.04, 862
See application file for complete search history.

(56) References Cited

U.S. PATENT DOCUMENTS 3,693,432 A * 9/1972 Stewart .................. G01N 3/307
73/12.05
5,565,626 A * 10/1996 Davie ........................ G01N 3/30
73/579
(Continued)

FOREIGN PATENT DOCUMENTS

DE 102005044403 9/2006
EP 0439998 8/1991
WO 2005043175 5/2005

OTHER PUBLICATIONS

European Patent Office, "Extended European Search Report from EP Application No. 15155143.9 mailed Jun. 23, 2015", from Foreign Counterpart of U.S. Appl. No. 14/189,777, filed Jun. 23, 2015, Published in: EP.

(Continued)

*Primary Examiner* — Lisa Caputo
*Assistant Examiner* — Nigel Plumb
(74) *Attorney, Agent, or Firm* — Fogg & Powers LLC (57) ABSTRACT A muzzle exit tester system comprises a barrel having an input end and an exit end, a shock plunger freely movable within the barrel, and a shock plate having a first side that faces the exit end of the barrel. A support isolation structure resiliently supports the shock plate, and receives a portion of the barrel that includes the exit end of the barrel. A pneumatic shock apparatus is operatively coupled to the input end of the barrel. The pneumatic shock apparatus is configured to retract the plunger in the barrel via a vacuum while producing a gas pressure charge, and subsequently release the gas pressure charge, such that the plunger accelerates to the exit end of the barrel and impacts the shock plate. The shock plate is configured to resonate at frequencies and amplitudes corresponding to a shock condition of a gun muzzle exit when impacted by the plunger.

20 Claims, 6 Drawing Sheets (51) Int. Cl.
  *F41B 11/681* (2013.01)
  *F41B 11/723* (2013.01)
  *F41B 11/87* (2013.01)

(56) References Cited

U.S. PATENT DOCUMENTS

| | | | | |
|---|---|---|---|---|
| 6,634,209 B1* | 10/2003 | Kastendieck | ............ | F41A 31/00 73/12.07 |
| 8,166,797 B2* | 5/2012 | Mooty | ................ | G01N 3/307 73/12.11 |
| 8,306,796 B2* | 11/2012 | Lee | ................ | G01M 7/022 703/6 |
| 8,430,670 B2* | 4/2013 | Landies | ................ | F41A 33/00 434/16 |
| 8,479,557 B2* | 7/2013 | Bottlinger, Jr. | ........ | G01N 3/313 73/12.01 |
| 2005/0092060 A1* | 5/2005 | Koland | ................ | G01P 21/00 73/12.01 |
| 2010/0199745 A1 | 8/2010 | Mooty et al. | | |

OTHER PUBLICATIONS

Binder et al., "Development of a Pyrotechnic Shock Simulation Apparatus for Spacecraft Applications", Jun. 10, 2012, pp. 1-17, Publisher: American Institute of Aeronautics and Astronautics.

Irvine, "An Introduction to the Shock Response Spectrum", Jul. 9, 2012, pp. 1-28.

"Little Mountain Test Facility", 2010, pp. 1-36, Publisher: The Boeing Company, Published in: Ogden, UT.

"Pyroshock Testing", pp. 1-4, Publisher: MGA Research Corporation.

Titulaer et al., "An Alternative to Pyrotechnic Testing for Shock Identification", "2007 IMAC-XXV: Conference & Exposition on Structural Dynamics", 2007, pp. 1-11.

* cited by examiner

MUZZLE EXIT TESTER

BACKGROUND

Navigational guidance devices are an integral part of smart munitions, which can be implemented as rockets, missiles, and bombs. Until recently, these guidance devices have had insufficient techniques to test their survivability and functionality in a laboratory setting. For example, high speed centrifuges (at tens of thousands of G's) allow for testing of low frequency quasi-static loads applied to guidance devices during the initial phase of gun or rocket launch. In addition, solenoid actuated mechanical impact shock and pyroshock have been used to simulate the dynamics of fin deployment. Vibration and low G centrifuge have also been used to test maneuvering of the projectile during its mission.

Nevertheless, there are few good options for testing the high amplitude, high frequency dynamic shock environment that is caused by hot propellant gases expanding as the projectile leaves the gun barrel or muzzle. One laboratory method intended to replicate the muzzle exit shock is a pyrotechnic shock, but this method has several shortcomings. This method requires expendable explosive materials, and can also be destructive to test holding fixtures. In addition, this method requires a long lead time for setup (e.g., months), has poor repeatability, has difficulty in tuning the shock profile, and results in high measurement errors.

Another laboratory method uses pneumatics to produce the shock. A unit under test is exposed to the shock as a deceleration upon impact of the unit and a honeycomb or other deformable structure downstream. Often times in pneumatic shock applications, a section of a barrel is required to be under vacuum in order for the unit under test to reach a high enough velocity. This requires a disposable membrane to be punctured as a pressure barrier during the test. That particular pneumatic method is undesirable because it requires to dispose and replace test equipment parts.

Another muzzle exit testing option is to use the U.S. Army's soft catch howitzer gun (SCat gun) at the Picatinny Arsenal or similar test facilities. This option, however, is an overtest due to soft catch mechanisms, has a high cost, does not include a unit under test power on sequence, does not have a quick turn around on data collection (weeks), allows only for a small sample size, and does not only test the muzzle exit portion of the mission timeline.

Further methods of muzzle exit testing include field testing, such as proving ground testing or flight testing. These methods, however, have high risk, high cost, limited repeatability, and high visibility due to testing at the customer level. In addition, field testing requires a unit under test to be mounted within an expendable projectile, burns propellant to accelerate, may require an expendable method of stopping the projectile, or may not return a functional or structurally intact unit under test, for further testing and observation, due to impact damage. In addition, waiting to test shock robustness until a flight test can cost over one million dollars for the test, plus heightened visibility, and if a failure occurs, a costly amount of product redevelopment is required.

SUMMARY

A muzzle exit tester system comprises a barrel having an input end and an exit end, a shock plunger freely movable within the barrel, and a shock plate having a first side that faces the exit end of the barrel. A support isolation structure resiliently supports the shock plate, and receives a portion of the barrel that includes the exit end of the barrel. A pneumatic shock apparatus is operatively coupled to the input end of the barrel. The pneumatic shock apparatus is configured to retract the shock plunger in the barrel via a vacuum while producing a gas pressure charge, and subsequently release the gas pressure charge, such that the shock plunger accelerates to the exit end of the barrel and impacts the shock plate. The shock plate is configured to resonate at frequencies and amplitudes corresponding to a shock condition of a gun muzzle exit when impacted by the shock plunger.

BRIEF DESCRIPTION OF THE DRAWINGS

Features of the present invention will become apparent to those skilled in the art from the following description with reference to the drawings. Understanding that the drawings depict only typical embodiments and are not therefore to be considered limiting in scope, the invention will be described with additional specificity and detail through the use of the accompanying drawings, in which.

DETAILED DESCRIPTION

In the following detailed description, embodiments are described in sufficient detail to enable those skilled in the art to practice the invention. It is to be understood that other embodiments may be utilized without departing from the scope of the invention. The following detailed description is, therefore, not to be taken in a limiting sense.

A testing system is provided that replicates a muzzle exit shock produced during a gun launch, while in a laboratory setting. The muzzle exit (also known as the "set-forward") event is the short duration transient shock created by the expansion of hot propellant gases and the exit of a projectile from the end of a gun muzzle or barrel, such as occurs with a SCat gun, tank gun, or howitzer gun. These shocks contain high frequency energy that creates a shock response in the projectile that has high levels of stress particularly in frequency ranges important to navigational sensors, such as an inertial measurement unit (IMU) or global positioning system (GPS) sensors.

The present muzzle exit tester system employs the dynamics of forced input and resonant plate technologies, to repeatedly and accurately reproduce a muzzle exit shock. The resonant plate technology can be used to create a shock response spectrum similar to a field environment in the laboratory. This allows for testing of various devices at customized shock response spectrum levels.

The testing system generally includes a barrel, a shock plunger freely movable within the barrel, a shock plate that faces an exit end of the barrel, and a pneumatic shock apparatus coupled to an input end of the barrel. A mounting adapter can be implemented on the shock plate to mount a unit under test (UUT), such as an accelerometer, a gyroscope, an IMU, a GPS sensor, or other electronic or mechanical device. The shock plate can be designed to resonate at frequencies and amplitudes that match various shock specifications. Further, customized shock response spectrum levels can be created based on the designs of the shock plate and plunger.

During operation of the muzzle exit tester, the pneumatics are used to retract the shock plunger within the barrel via a vacuum while producing a gas pressure charge, which is then released into the input end of the barrel to cause the shock plunger to accelerate through the barrel and impact the shock plate. A shock response is then measured and recorded.

Alternatively, non-contact measurement of acceleration on the shock plate can be implemented such as with a laser Doppler vibrometer. The laser Doppler vibrometer shines laser light on a surface of the shock plate to measure acceleration during impact of the shock plate. The laser Doppler vibrometer can be used simultaneously with high speed video to measure displacement of the shock plate. This approach is advantageous for shock amplitudes that are great enough to damage accelerometers, as well as for making measurements on the UUT that are either size restrictive for using accelerometers or sensitive to mass loading.

The muzzle exit tester can be automated and operated via a processing device such as a programmable logic controller (PLC), which is configured to control pneumatics such as solenoid pressure valves to perform pneumatic shock testing. In general, the PLC controls the pneumatic process timing.

In one embodiment, the PLC controls a safety valve, releasing all pressure on a power outage or abort command. The PLC also controls the timing of a charge valve, effectively controlling the input pressure to the system. The PLC further controls the timing of a vacuum valve, effectively controlling the plunger pull back and the post-shock pressurization relief. In addition, the PLC controls the timing of a release valve, effectively controlling the volume of pressurized gas released and the duration of the pressurization impulse.

A safety structure can also be built around the testing system station. The safety structure can be configured for structural retention of pressurized air and possible debris, and can include windows for high speed video and laser Doppler vibrometer access. A locking door can be employed for quickly changing out UUTs, and safety interlocks can be used to depower and depressurize the system. The safety structure can also include an exhaust vent to disperse pressurized gas above head level, a backstop to prevent plunger backfire in the case of barrel flange failure, and a vacuum relief valve to return the system to ambient conditions.

A UUT data computer can be implemented into the present system that allows operational data to be collected and recorded before, during, and after testing. In one embodiment, a UUT data acquisition station can be integrated into the system in order to create a mission timeline power-on sequence and collect UUT performance data. This is highly advantageous for testing UUT design iterations. In addition, automated data acquisition scripts and analyses can be used to process data.

The present muzzle exit tester system has many advantages and benefits. For example, the tester system is self-contained, has a quick set-up time, and employs a reusable plunger to transfer pneumatic energy into kinetic energy. The use of pneumatic energy, as opposed to explosive energy, allows the system to withstand thousands of shock tests.

The muzzle exit tester system can be used to create a very repeatable shock profile. Once the necessary variables are set, no further adjustments are needed, and data produced by the shocks is immediately available.

In addition, the muzzle exit tester system uses entirely reusable parts and is not destructive to the test station, removing the need for replaceable parts. This substantially lowers the cost compared to conventional test systems. The use of materials that are not destructively damaged during testing keeps recurring operating costs to a minimum. In addition, as the UUT can be mounted to the shock plate and accelerates due to the impact of the plunger and shock plate, an expendable projectile or propellant to create motion is not required.

The present system also employs a spring isolation structure, which over time dampens out the motion of the shock plate. This precludes the need for expendable capture mechanisms. Further, many of the test system components can be purchased off the shelf, further reducing costs.

The tester system allows many units and/or configurations to be tested in short order, as the test lab can be in the same location as a manufacturing facility. In addition, a substantially reduced number of support staff is needed to run the tester system.

Further aspects of the muzzle exit tester system are described hereafter with reference to the drawings.

Figure 1:
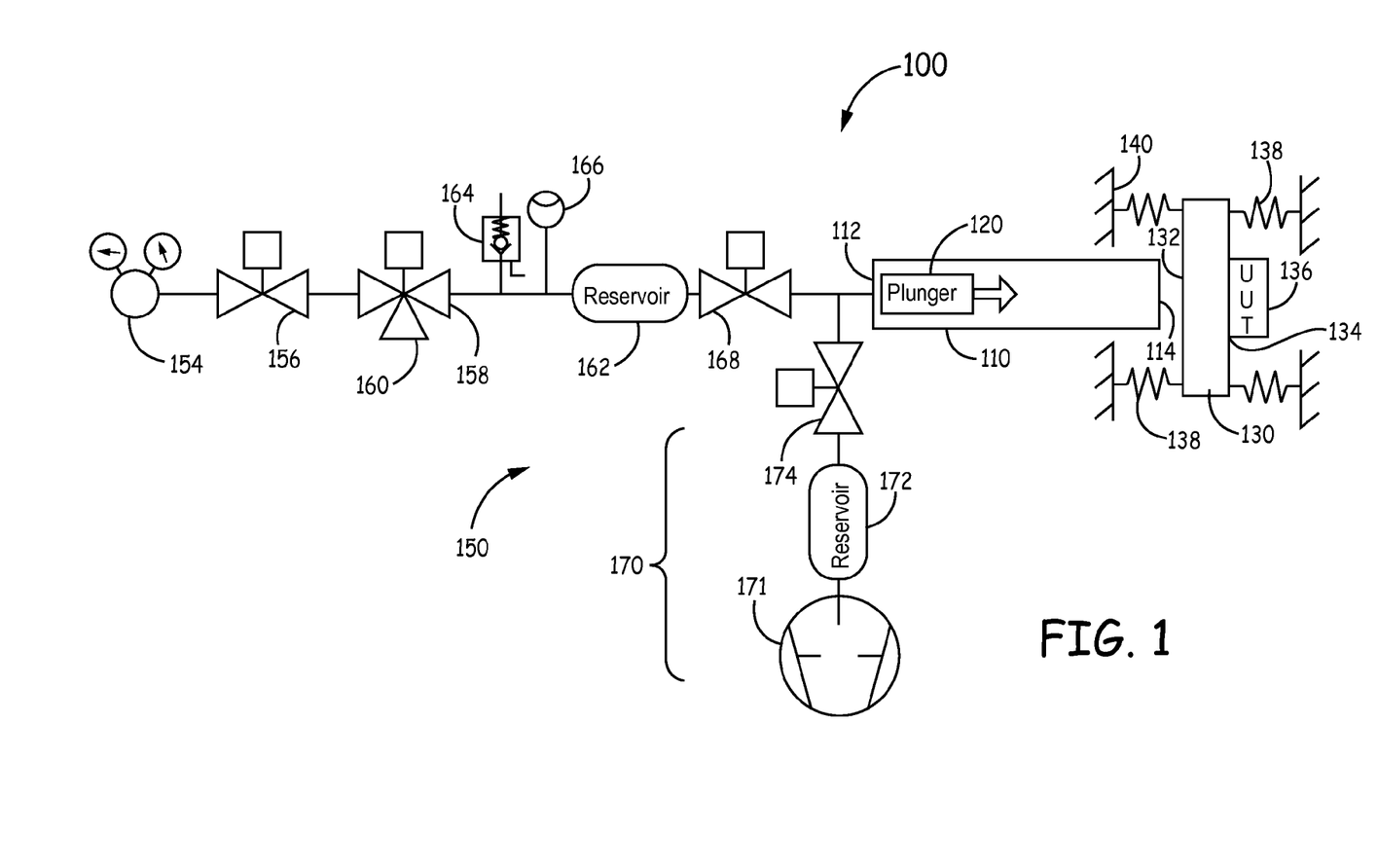
FIG. 1 is a schematic diagram of a muzzle exit tester system according to one embodiment.

FIG. 1 is a schematic diagram of a muzzle exit tester system 100 according to one embodiment. The muzzle exit tester system 100 generally includes a barrel 110, a shock plunger 120 freely movable within barrel 110, a shock plate 130 facing one end of barrel 110, and a support isolation structure 140 for shock plate 130. The muzzle exit tester system 100 also includes a pneumatic shock apparatus 150 operatively coupled to barrel 110. Each of these components of muzzle exit tester system 100 are described in further detail hereafter.

In one embodiment, barrel 110 is a cylindrical tube having an input opening at a proximal end 112 and an exit opening at a distal end 114. The barrel 110 can be constructed of a metal material such as steel and is configured to provide the kinetic energy required to replicate a muzzle exit shock. The design of barrel 110 leads to the creation of an impact. The interior circumference barrel 110 is smooth and straight enough to prevent plunger 120 from binding while it travels the length of barrel 110. Since barrel 110 is open ended and not evacuated, there is a column of air that acts as a spring that will work against the motion of the plunger. To circumvent this issue, vent holes can be added to the barrel along a portion of its length that is inside isolation structure 150. In addition, a gap can be created between distal end 114 of barrel 110 and shock plate 130. The vent holes and gap allow for the upstream air to exhaust out of the way of plunger 120. The vent holes, along with a post-shock vacuum, exhaust pressurized air from behind plunger 120 as it bounces back after the shock impact, preventing plunger 120 from a double hit. The input opening at proximal end 112 of barrel 110 can be capped with a sealed flange to prevent leakage of the pressurized air used to accelerate plunger 120.

Figure 5:
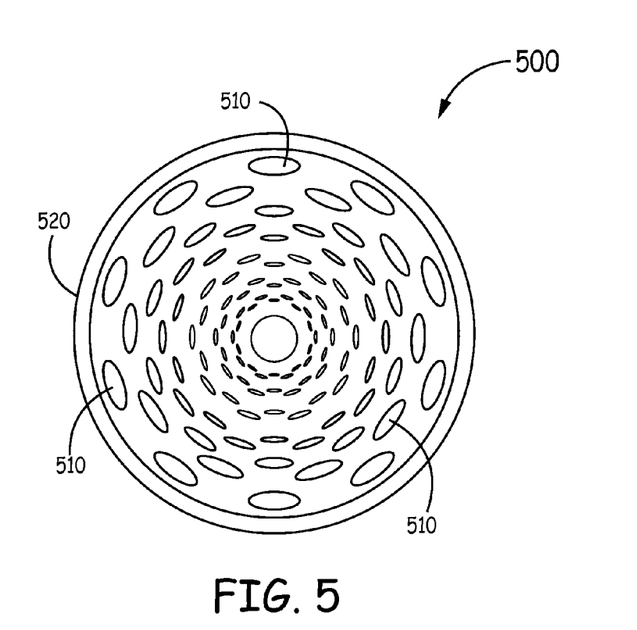
FIG. 5 is an end view of a barrel employed in a muzzle exit tester system according to one embodiment.

An exemplary embodiment of the barrel is shown in FIG. 5, which is described in further detail hereafter.

In one embodiment, shock plunger 120 has a generally cylindrical shape and as is sized to move freely within barrel 110. The design of shock plunger 120 is integral to the shock response. The material selection for the impact tip of plunger 120 affects the frequency content that is transferred to shock plate 130. Hard materials such as metals produce a higher frequency response, and softer materials such as rubber produce a lower frequency response. Materials with a natural frequency near the required peak in a specified shock response spectrum should be selected for the impact tip. In addition, the material for the impact tip needs to be resilient enough to withstand multiple shocks.

The radius of the impact tip of plunger 120 is another consideration that affects the frequency content transferred to the shock plate by changing the impact pulse duration. A purely flat tip will produce the shortest duration impulse and result in higher frequency content, whereas a rounded tip will produce a longer duration impulse and result in lower frequency content. Mass is another consideration for the design of plunger 120. Adding mass will lower the frequency content by lengthening the impact pulse duration. Removing mass will increase the frequency content of the shock response spectrum.

Figure 6:
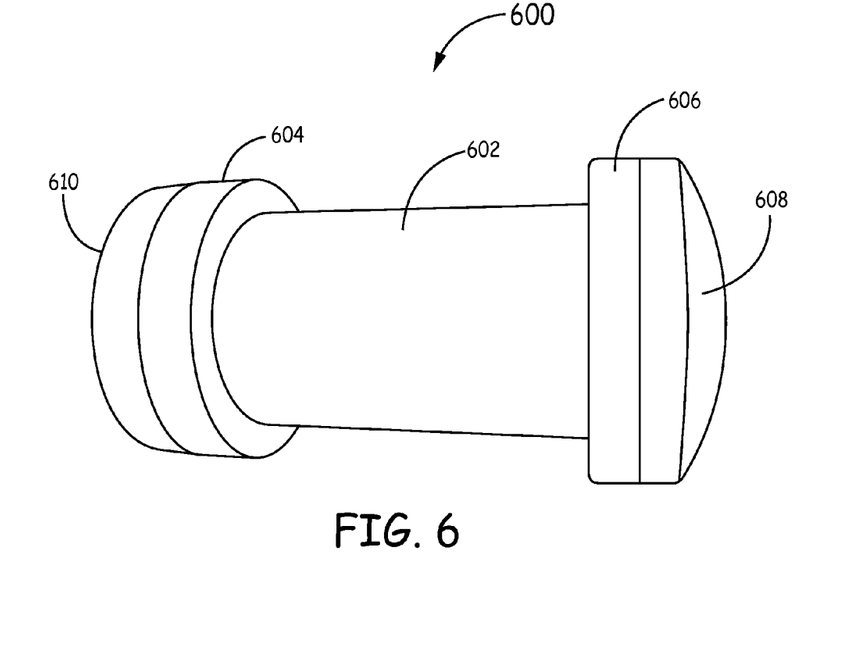
FIG. 6 is a perspective view of a shock plunger employed in a muzzle exit tester system according to one embodiment.

An exemplary embodiment of the shock plunger is shown in FIG. 6, which is described in further detail hereafter.

In one embodiment, shock plate 130 has a generally rectangular shape and can be made of aluminum. A strike plate 132, such as a steel plate, can be located on the side of shock plate 130 that faces distal end 114 of barrel 110 to improve shock plate durability. A mounting structure 134 such as a steel mount is located on the opposite side of shock plate 130 for mounting a UUT 136. The shock plate 130 can be isolated from the other system components by a set of springs 138, which resiliently couple shock plate 130 to support isolation structure 140. The shock plate 130 is configured to absorb the shock of impact from shock plunger 120. In addition, shock plate 130 can be designed to resonate at frequencies and amplitudes that match various shock specifications as needed.

The support isolation structure 140 can be made of a metal material such as steel, and can include an opening for visualization and exhaust to prevent overpressure during operation. The springs 138 can be high strength die springs that are capable of absorbing the high energy transferred to shock plate 130, and damping the shock response down to zero motion in a non-destructive manner. The isolation structure 140 can also be implemented with strategically placed windows in which to view the motion of shock plate 130 via high speed video.

Figure 7:
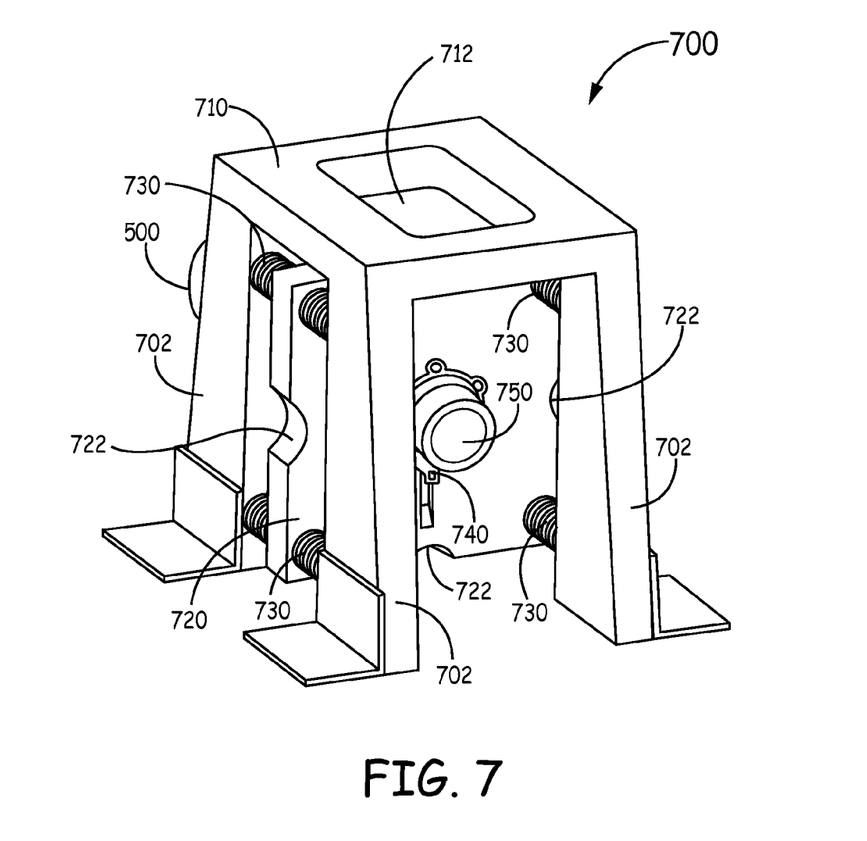
FIG. 7 is a perspective view of a support isolation structure for a shock plate employed in a muzzle exit tester system according to one embodiment.

An exemplary embodiment of the support isolation structure and shock plate is shown in FIG. 7, which is described in further detail hereafter.

The pneumatic shock apparatus 150 is coupled to a source of pressurized gas, such as facility clean dry pressurized air, which is used to power the pneumatic components. As illustrated in FIG. 1, pneumatic shock apparatus 150 includes a pressure regulator 154, a charge valve 156, such as a solenoid charge valve, which is in communication with pressure regulator 154, and a safety valve 158 having a vent 160, which is communication with charge valve 156. The pressure regulator 154 is configured to pass pressurized air to charge valve 156, which in turn is configured to pass the pressurized air to safety valve 158. A pressure reservoir 162 is in communication with safety valve 158 and is configured to receive and contain the pressurized air until needed. A pressure relief device 164 and a pressure indicator 166 can be coupled between safety valve 158 and pressure reservoir 162. A release valve 168, such as a solenoid release valve, is in communication with an outlet of pressure reservoir 162. An outlet of release valve 168 is in communication with the input opening of barrel 110 at proximal end 112.

The pneumatic shock apparatus 150 also includes a vacuum assembly 170, which includes a vacuum pump 171, and a vacuum reservoir 172 in communication with vacuum pump 171. A vacuum valve 174, such as a solenoid vacuum valve, is in communication with vacuum reservoir 172 and the input opening of barrel 110 at proximal end 112. The vacuum assembly 170 provides suction for retracting shock plunger 120 back toward the input opening of barrel 110 to the set position. This can be done between shock tests to minimize setup time. The vacuum assembly 170 also relieves pressure behind the plunger post-shock to prevent repressurization and a double impact of the plunger.

Figure 2:
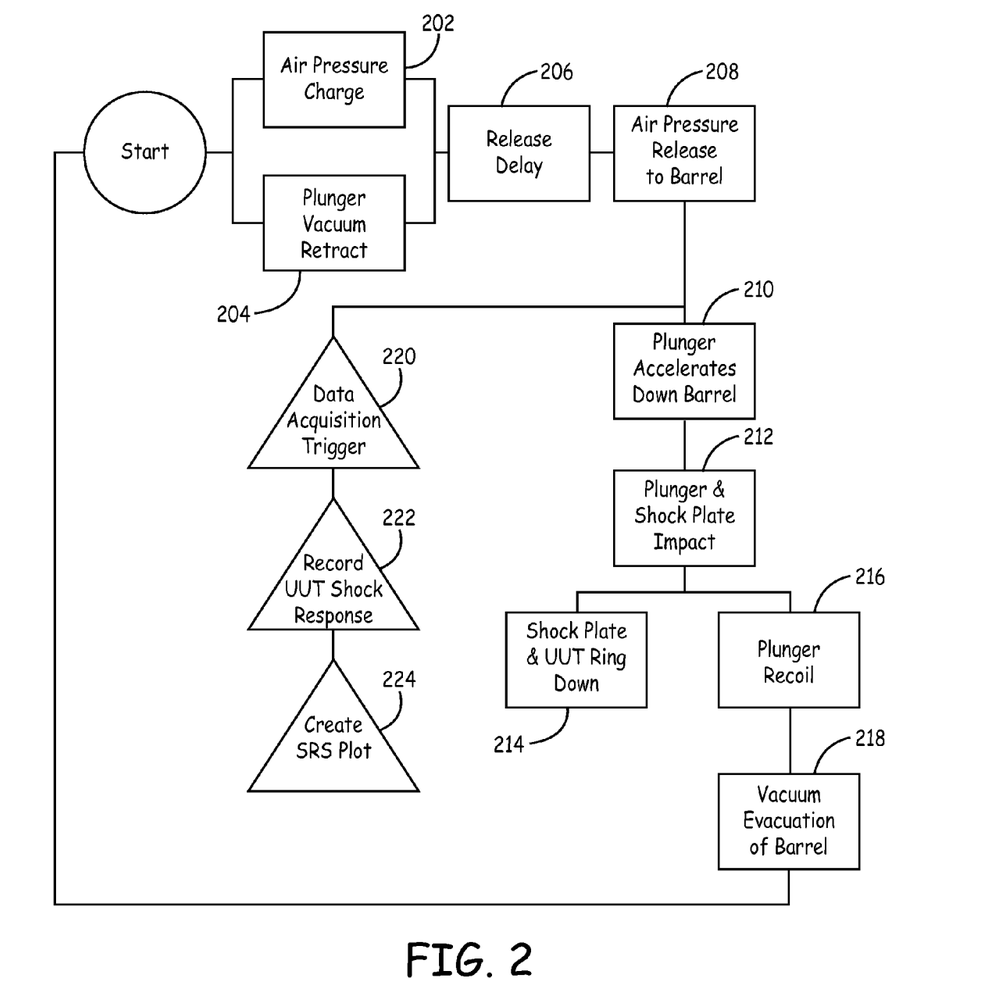
FIG. 2 is a process flow diagram showing the operation of a muzzle exit tester system according to one embodiment.

FIG. 2 is a process flow diagram showing the operation of a muzzle exit tester system, such as tester system 100. At the start, air pressure is charged (block 202), such as by using pressure regulator 154, charge valve 156, and safety valve 158, to direct pressurized air to pressure reservoir 162. At the same time, a shock plunger such as plunger 120 is vacuum retracted (block 204), for example by using vacuum assembly 170. After a release delay (block 206), air pressure is released to a barrel such as barrel 110 (block 208), for example, by using release valve 168. This causes the shock plunger to accelerate down the barrel (block 210) and impact a shock plate such as plate 130 (block 212). This is followed by ring down of the shock plate and a UUT (block 214) at specific frequencies. At the same time, the shock plunger is recoiled within the barrel (block 216). Vacuum evacuation of the barrel then occurs (block 218), and the process can be started again. Once air pressure is released to the barrel, a data acquisition trigger can be actuated (block 220). The UUT shock response is recorded (block 222) after impact of the shock plunger with the shock plate, and a shock response spectrum plot can be created (block 224).

Figure 3:
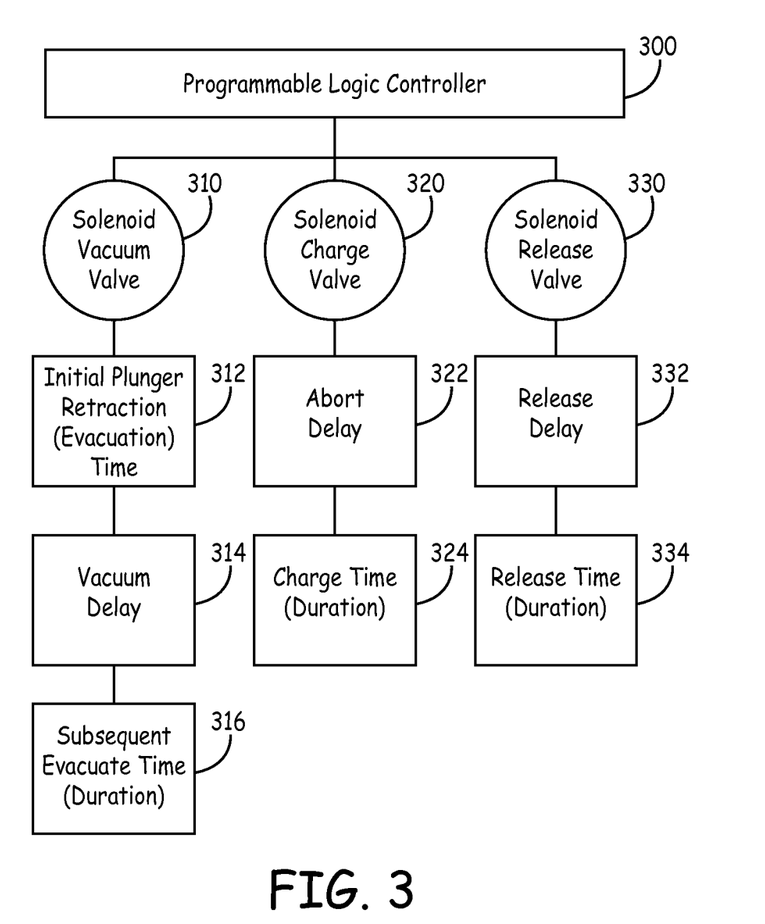
FIG. 3 is a block diagram showing the control functions of a programmable logic controller implemented with a muzzle exit tester system according to one embodiment.

In one embodiment, the pneumatic shock apparatus of a muzzle exit tester system, such as tester system 100, can be operated via a Programmable Logic Controller (PLC) 300, as depicted in FIG. 3. The PLC 300 can be programmed to control various solenoid pressure valves, including a solenoid vacuum valve 310, a solenoid charge valve 320, and a solenoid release valve 330. The valves can be coupled to an AC power source. A safety switch can be used to enable/disable the AC power to the valves as needed.

The PLC 300 controls the initial plunger retraction (evacuation) time (block 312), the vacuum delay (block 314), and the subsequent evacuate time (duration) (block 316) of vacuum valve 310. The PLC 300 also controls the abort delay (block 322), and the charge time (duration) (block 324) of charge valve 320. The PLC 300 further controls the release delay (block 332), and release time (duration) (block 334) of release valve 330.

Figure 4:
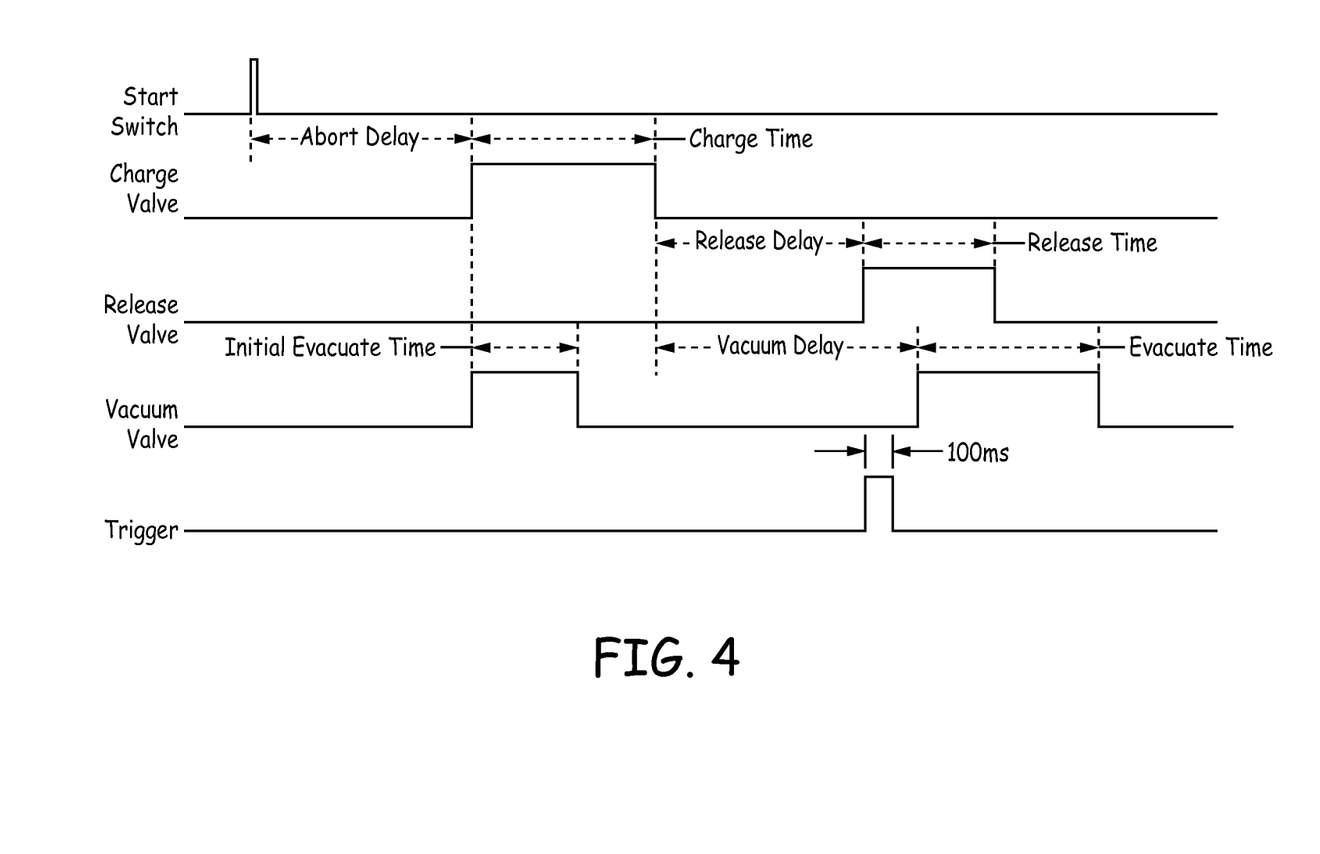
FIG. 4 is a timing diagram for process sequencing of a pneumatic shock apparatus implemented with a programmable logic controller in a muzzle exit tester system according to one embodiment.

An exemplary timing diagram for process sequencing of the pneumatic shock apparatus with PLC 300 is shown in FIG. 4. The timing sequences for a start switch, the charge valve, the release valve, the vacuum valve, and a trigger are depicted. An abort delay occurs between actuation of the start switch and the beginning of the charge time with actuation of the charge valve. A release delay occurs between the end of the charge time and the beginning of the release time with actuation of the release valve. An initial evacuate time begins at the start of the charge time with actuation of the vacuum valve, but does not exceed the duration of the charge time. A vacuum delay starts at the end of the charge time and extends past the start of the release time. A subsequent evacuate time starts at the end of the vacuum delay and extends past the end of the release time. A trigger can be actuated for a specified time, such as 100 ms for example, to actuate the release valve.

FIG. 5 illustrates an exemplary embodiment of a cylindrical barrel 500, which can be employed in the muzzle exit tester system. The barrel 500 has a plurality of vent holes 510 around its circumference along a distal end section 520. The vent holes 510 reduce pressure within the barrel during operation, which provides for a controlled impact of the shock plunger on the shock plate.

FIG. 6 illustrates an exemplary embodiment of a shock plunger 600, which can be employed in the muzzle exit tester system. The shock plunger 600 is generally shaped similar to a dumbbell, having a narrower cylindrical mid section 602 between two wider cylindrical end sections 604 and 606. The shock plunger 600 is sized to move freely within barrel 500 (FIG. 5). The end sections 604 and 606 provide guidance for plunger 600 as it travels down barrel 500 while preventing binding. The shape of plunger 600 also allows for convenient addition or removal of mass to mid section 602 to affect the shock response spectrum.

The end section 606 includes an impact tip 608 that is configured to contact a shock plate. The size, shape, and material of impact tip 608 can be changed as needed in order to obtain a desired shock response spectrum. For example, the radius and mass of impact tip 608 can be changed in order to tune the duration of the impact. The end section 604 includes a seat tip 610 that is configured to allow plunger 600 to be seated within barrel 500 after vacuum retraction of plunger 600. The material of seat tip 610 can be selected to provide durability for repeated vacuum retractions of plunger 600. In one embodiment, impact tip 608 can be a fiberglass material, seat tip 610 can be a plastic material, end sections 604 and 606 can be made of aluminum, and mid section 602 can include a brass material.

FIG. 7 illustrates an exemplary embodiment of a support isolation structure 700 for a shock plate 720, which can be employed in the muzzle exit tester system. The isolation structure 700 has a plurality of legs 702, which support a roof structure 710 having an opening 712 for exhaust and visualization purposes. The shock plate 720 has a generally rectangular shape and is suspended in the space between legs 702 by a set of rods that extend through each corner of shock plate 720 into legs 702. The rods also support a set of springs 730, such as die springs, which are located between each corner of shock plate 720 and legs 702. The rods provide linear guidance resulting in mainly unidirectional motion of shock plate 720. The springs 730 are configured to aid in absorbing the force of the shock when shock plate 720 is impacted. A set of spacers can be employed on the rods that retain a preload on springs 738, preventing any gaps from forming or non-linear acceleration caused by metal on metal impacts.

A mounting structure 740 is located on one side of shock plate 720 for mounting a UUT 750. The mounting structure 740 can include a UUT mounting adapter plate that provides durability to the mounting holes in shock plate 720, and allows for swapping of different products and UUTs. The mounting structure 740 can also have an integrated accelerometer mount for shock measurement. A strike plate can be located on the side of shock plate 720 opposite from mounting structure 740. The strike plate provides a durable interface between shock plate 720 and plunger 600 (FIG. 6) during impact.

The dimensions and shape of shock plate 720 can be selected to create resonances that when excited produce a desired shock response spectrum. For example, scalloped indentations 722 can be located along opposite vertical and horizontal edges of shock plate 720. This shape provides for selected resonant frequencies to be excited during the shock to create the desired shock response spectrum.

The isolation structure 700 is configured to receive distal end section 520 of barrel 500 (FIG. 5), which faces the side of shock plate 720 opposite from the side where UUT 750 is mounted. The isolation structure 700 is designed to withstand the forces exerted by the movement of shock plate 720.

Example Embodiments

Example 1 includes a muzzle exit tester system, comprising: a barrel having an input end and an exit end; a shock plunger freely movable within the barrel; a shock plate having a first side that faces the exit end of the barrel; a support isolation structure that resiliently supports the shock plate, and receives a portion of the barrel that includes the exit end of the barrel; and a pneumatic shock apparatus operatively coupled to the input end of the barrel, the pneumatic shock apparatus configured to retract the shock plunger in the barrel via a vacuum while producing a gas pressure charge, and subsequently release the gas pressure charge, such that the shock plunger accelerates to the exit end of the barrel and impacts the shock plate; wherein the shock plate is configured to resonate at frequencies and amplitudes corresponding to a shock condition of a gun muzzle exit when impacted by the shock plunger.

Example 2 includes the system of Example 1, wherein the barrel comprises a cylindrical tube having a plurality of vent holes located around the portion of the barrel received in the isolation structure.

Example 3 includes the system of any of Examples 1-2, wherein the shock plunger has a cylindrical dumbbell shape.

Example 4 includes the system of any of Examples 1-3, wherein the shock plate includes a mounting structure for attaching a unit under test on a second side of the shock plate opposite from the first side.

Example 5 includes the system of any of Examples 1-4, wherein the shock plate includes a strike plate on the first side that faces the exit end of the barrel.

Example 6 includes the system of any of Examples 1-5, wherein the support isolation structure comprises: a plurality of legs; a roof structure supported by the legs and having an opening for exhaust and visualization; a set of die springs coupled to each of the legs and the shock plate; wherein the shock plate is located between the legs of the support isolation structure.

Example 7 includes the system of any of Examples 1-6, wherein the pneumatic shock apparatus comprises: a pressure regulator; a charge valve in communication with the pressure regulator; a safety valve in communication with the charge valve; a pressure reservoir in communication with the safety valve; and a release valve in communication with the pressure reservoir and the input end of the barrel.

Example 8 includes the system of any of Examples 1-7, wherein the pneumatic shock apparatus further comprises a vacuum assembly comprising: a vacuum pump; a vacuum reservoir in communication with the vacuum pump; and a vacuum valve in communication with the vacuum reservoir and the input end of the barrel; wherein the vacuum assembly provides suction for retracting the shock plunger toward the input end of the barrel.

Example 9 includes the system of any of Examples 1-8, wherein the pneumatic shock apparatus further comprises a pressure relief device and a pressure indicator.

Example 10 includes the system of any of Examples 8-9, wherein the pneumatic shock apparatus further comprises a programmable logic controller operatively coupled to the vacuum valve, the charge valve, the safety valve, and the release valve.

Example 11 includes the system of any of Examples 8-10, wherein the vacuum valve, the charge valve, the safety valve, and the release valve each comprises a solenoid valve.

Example 12 includes a muzzle exit testing method, comprising: providing a muzzle exit tester comprising: a barrel having an input end and an exit end; a shock plunger freely movable within the barrel; and a shock plate having a first side that faces the exit end of the barrel; retracting the shock plunger within the barrel via a vacuum; producing a gas pressure charge; releasing the gas pressure charge into the input end of the barrel to cause the shock plunger to accelerate through the barrel to the exit end and impact the first side of the shock plate; and measuring a shock response of the shock plate after impact of the shock plunger with the first side of the shock plate.

Example 13 includes the method of Example 12, wherein the shock plate resonates at frequencies and amplitudes corresponding to a shock condition of a gun muzzle exit when impacted by the shock plunger.

Example 14 includes the method of any of Examples 12-13, further comprising: mounting a unit under test (UUT) on a second side of the shock plate opposite from the first side prior to retracting the shock plunger.

Example 15 includes the method of Example 14, wherein the UUT comprises an accelerometer, a gyroscope, an inertial measurement unit, or a global positioning system sensor.

Example 16 includes the method of any of Examples 12-13, wherein the shock response of the shock plate is measured with a laser Doppler vibrometer.

Example 17 includes the method of any of Examples 12-16, wherein the muzzle exit tester is automated and operated via a programmable logic controller that controls solenoid pressure valves in a pneumatic shock apparatus.

Example 18 includes the method of Example 17, wherein the solenoid pressure valves comprise a vacuum valve, a charge valve, a release valve, and a safety valve.

Example 19 includes the method of Example 18, wherein the programmable logic controller is configured to: control timing of the vacuum valve to retract the shock plunger within the barrel and provide post-shock pressurization relief; control timing of the charge valve to produce the gas pressure charge; control timing of the release valve to release the gas pressure charge into the input end of the barrel; and actuate the safety valve to release all gas pressure on a power outage or abort command.

Example 20 includes the method of any of Examples 12-19, wherein operational data is collected and recorded before, during, and after the shock response of the shock plate.

The present invention may be embodied in other specific forms without departing from its essential characteristics. The described embodiments are to be considered in all respects only as illustrative and not restrictive. The scope of the invention is therefore indicated by the appended claims rather than by the foregoing description. All changes that come within the meaning and range of equivalency of the claims are to be embraced within their scope.

What is claimed is:

1. A muzzle exit tester system, comprising:
    a barrel having an input end and an exit end;
    a shock plunger freely movable within the barrel;
    a shock plate having a first side that faces the exit end of the barrel;
    a support isolation structure that resiliently supports the shock plate, and receives a portion of the barrel that includes the exit end of the barrel; and
    a pneumatic shock apparatus operatively coupled to the input end of the barrel, the pneumatic shock apparatus configured to retract the shock plunger in the barrel via a vacuum while producing a gas pressure charge, and subsequently release the gas pressure charge, such that the shock plunger accelerates to the exit end of the barrel and impacts the shock plate;
    wherein the shock plate is dimensioned and shaped with selected geometries and cutouts to create resonances that when excited produce a desired shock response spectrum;
    wherein the shock plate is configured to resonate at frequencies and amplitudes corresponding to a shock condition of a gun muzzle exit when impacted by the shock plunger.

2. The system of claim 1, wherein the barrel comprises a cylindrical tube having a plurality of vent holes located around the portion of the barrel received in the isolation structure.

3. The system of claim 1, wherein the shock plunger has a cylindrical dumbbell shape.

4. The system of claim 1, wherein the shock plate includes a mounting structure for attaching a unit under test on a second side of the shock plate opposite from the first side.

5. The system of claim 1, wherein the shock plate includes a strike plate on the first side that faces the exit end of the barrel.

6. The system of claim 1, wherein the support isolation structure comprises:
    a plurality of legs;
    a roof structure supported by the legs and having an opening for exhaust and visualization; and
    a set of die springs coupled to each of the legs and the shock plate;
    wherein the shock plate is located between the legs of the support isolation structure.

7. The system of claim 1, wherein the pneumatic shock apparatus comprises:
    a pressure regulator;
    a charge valve in communication with the pressure regulator;
    a safety valve in communication with the charge valve;
    a pressure reservoir in communication with the safety valve; and
    a release valve in communication with the pressure reservoir and the input end of the barrel.

8. The system of claim 7, wherein the pneumatic shock apparatus further comprises a vacuum assembly comprising:
    a vacuum pump;
    a vacuum reservoir in communication with the vacuum pump; and
    a vacuum valve in communication with the vacuum reservoir and the input end of the barrel;
    wherein the vacuum assembly provides suction for retracting the shock plunger toward the input end of the barrel.

9. The system of claim 7, wherein the pneumatic shock apparatus further comprises a pressure relief device and a pressure indicator.

10. The system of claim 8, wherein the pneumatic shock apparatus further comprises a programmable logic controller operatively coupled to the vacuum valve, the charge valve, the safety valve, and the release valve.

11. The system of claim 10, wherein the vacuum valve, the charge valve, the safety valve, and the release valve each comprises a solenoid valve.

12. A muzzle exit testing method, comprising:
    providing a muzzle exit tester comprising:
        a barrel having an input end and an exit end;
        a shock plunger freely movable within the barrel; and
        a shock plate having a first side that faces the exit end of the barrel;
        wherein the shock plate is dimensioned and shaped with selected geometries and cutouts to create resonances that when excited produce a desired shock response spectrum;
    retracting the shock plunger within the barrel via a vacuum;
    producing a gas pressure charge;

releasing the gas pressure charge into the input end of the barrel to cause the shock plunger to accelerate through the barrel to the exit end and impact the first side of the shock plate; and measuring a shock response of the shock plate after impact of the shock plunger with the first side of the shock plate.

13. The method of claim 12, wherein the shock plate resonates at frequencies and amplitudes corresponding to a shock condition of a gun muzzle exit when impacted by the shock plunger.

14. The method of claim 12, further comprising:

mounting a unit under test (UUT) on a second side of the shock plate opposite from the first side prior to retracting the shock plunger.

15. The method of claim 14, wherein the UUT comprises an accelerometer, a gyroscope, an inertial measurement unit, or a global positioning system sensor.

16. The method of claim 12, wherein the shock response of the shock plate is measured with a laser Doppler vibrometer.

17. The method of claim 12, wherein the muzzle exit tester is automated and operated via a programmable logic controller that controls solenoid pressure valves in a pneumatic shock apparatus.

18. The method of claim 17, wherein the solenoid pressure valves comprise a vacuum valve, a charge valve, a release valve, and a safety valve.

19. The method of claim 18, wherein the programmable logic controller is configured to:

control timing of the vacuum valve to retract the shock plunger within the barrel and provide post-shock pressurization relief;

control timing of the charge valve to produce the gas pressure charge;

control timing of the release valve to release the gas pressure charge into the input end of the barrel; and actuate the safety valve to release all gas pressure on a power outage or abort command.

20. The method of claim 12, wherein operational data is collected and recorded before, during, and after the impact of the shock plunger with the first side of the shock plate.

* * * * *